United States Patent
Khadir et al.

(10) Patent No.: US 10,248,168 B2
(45) Date of Patent: Apr. 2, 2019

(54) RELIGIOUS APPLICATION FOR MOBILE AND WEARABLE TECHNOLOGY DEVICES

(71) Applicants: Mateen-Mohammed Abdul Khadir, Chicago, IL (US); Asif Ahmed, Lisle, IL (US); Aijaz Ansari, Chicago, IL (US)

(72) Inventors: Mateen-Mohammed Abdul Khadir, Chicago, IL (US); Asif Ahmed, Lisle, IL (US); Aijaz Ansari, Chicago, IL (US)

(*) Notice: Subject to any disclaimer, the term of this patent is extended or adjusted under 35 U.S.C. 154(b) by 109 days.

(21) Appl. No.: 15/177,884

(22) Filed: Jun. 9, 2016

(65) Prior Publication Data

US 2016/0364999 A1 Dec. 15, 2016

Related U.S. Application Data

(60) Provisional application No. 62/173,154, filed on Jun. 9, 2015.

(51) Int. Cl.
| | |
|---|---|
| G09B 19/00 | (2006.01) |
| G06F 1/16 | (2006.01) |
| A47G 33/00 | (2006.01) |
| A63B 24/00 | (2006.01) |
| G06F 17/00 | (2019.01) |
| G06Q 50/00 | (2012.01) |
| G16H 20/00 | (2018.01) |

(52) U.S. Cl.
CPC .......... *G06F 1/1694* (2013.01); *A47G 33/00* (2013.01); *A47G 33/008* (2013.01); *A63B 24/0062* (2013.01); *G06F 17/00* (2013.01); *G06Q 50/00* (2013.01); *G16H 20/00* (2018.01); *A63B 2220/10* (2013.01)

(58) Field of Classification Search
CPC ..... G09B 19/003; G06F 1/1694; G06F 17/00; A47G 33/00; A47G 33/08; G06Q 50/00; A63B 24/0062; A63B 2220/10; G16H 20/00
See application file for complete search history.

(56) References Cited

U.S. PATENT DOCUMENTS

| | | | | |
|---|---|---|---|---|
| 6,202,035 B1* | 3/2001 | Lameer | ......... | G01C 21/20 342/443 |
| 6,783,822 B1* | 8/2004 | Faouaz | ......... | A47C 16/04 428/192 |
| 7,508,316 B1* | 3/2009 | Arrar | ......... | A47G 27/0237 340/502 |

(Continued)

*Primary Examiner* — Tramar Harper
*Assistant Examiner* — Malina D Blaise
(74) *Attorney, Agent, or Firm* — Sughrue Mion, PLLC

(57) ABSTRACT

Provided are systems and methods tracking a prayer session of a device user and notifying the device user regarding prayer session activity. The method includes receiving motion information from an accelerometer of the device, receiving altitude information from an altimeter of the device, and receiving position information from a gyroscope of the device while the device user is engaged in the prayer session. The method further includes determining a prayer unit number or prayer position based on one or more of the received motion information, altitude information, and position information, and notifying the device user of the determined prayer unit number or prayer position.

10 Claims, 15 Drawing Sheets
(15 of 15 Drawing Sheet(s) Filed in Color)

(56) References Cited

U.S. PATENT DOCUMENTS

| | | | |
|---|---|---|---|
| 8,898,012 B2* | 11/2014 | Mahmoud | G01C 21/08 701/408 |
| 9,750,977 B2* | 9/2017 | Yuen | A63B 24/0062 |
| 2005/0237859 A1* | 10/2005 | Jibrin | G04G 9/0076 368/47 |
| 2006/0068812 A1* | 3/2006 | Carro | H04M 1/72566 455/456.3 |
| 2007/0067054 A1* | 3/2007 | Danish | A47G 33/008 700/94 |
| 2009/0087825 A1* | 4/2009 | Govindswamy | G09B 19/00 434/245 |
| 2010/0120005 A1* | 5/2010 | Abouelsaadat | A47G 33/008 434/245 |
| 2011/0294100 A1* | 12/2011 | Jamal | A47G 27/0237 434/245 |
| 2016/0037482 A1* | 2/2016 | Higgins | H04W 68/005 455/414.1 |
| 2016/0213151 A1* | 7/2016 | Al-Saraj | A47C 7/02 |
| 2017/0266495 A1* | 9/2017 | DiBenedetto | A63B 24/0062 |
| 2018/0103859 A1* | 4/2018 | Provenzano | A61B 5/02438 |
| 2018/0174420 A1* | 6/2018 | Clark | G08B 21/0446 |

\* cited by examiner

RELIGIOUS APPLICATION FOR MOBILE AND WEARABLE TECHNOLOGY DEVICES

CROSS-REFERENCE TO RELATED PATENT APPLICATION

This application claims priority from U.S. Provisional Application No. 62/173,154 filed on Jun. 9, 2015, the disclosure of which is incorporated herein by reference in its entirety.

BACKGROUND

Technical Field

One or more exemplary embodiments relate to systems and methods for detecting prayer units while a device user is engaged in a prayer session comprising two or more prayer units, and more particularly to systems and methods for determining completion of each prayer unit and notifying the user, via the device, regarding completion of one or more prayer units.

Description of the Related Art

Activity tracking devices allow for tracking and monitoring a user's physical activity. For example, WO2011/028383 to Hoffman et al. discloses the collection and display of a user's athletic activity information while providing encouragement and maintaining the user's interest in continuing to perform the athletic activity. However, there has been no disclosure of systems, devices, or methods that are capable of tracking a user's prayer activity and providing the user with a detailed breakdown of the user's prayer activity.

SUMMARY

Muslims, followers of the teachings of the religion of Islam, are required to pray five times per day (at least) as one of the tenants of the religion. The five prayers include Fajr (dawn prayer), Dhuhr (noon prayer), Asr (afternoon prayer), Maghrib (sunset prayer), and Isha'a (night prayer). Each prayer session involves an individual performing a physical routine which includes first raising ones hands to their heads (Takbir) and then engaging in two or more rakats (prayer units). The number of rakats or prayer units depends on which of the five prayer sessions the individual is engaged in. The dawn prayer includes two obligatory prayer units, the noon prayer includes four obligatory prayer units, the afternoon prayer includes four obligatory prayer units, the sunset prayer includes three obligatory prayer units, and the night prayer includes four obligatory prayer units.

In addition to the five obligatory prayers, there are other prayers that Muslims perform, each of which also has a predetermined number of prayer units. One example is the offering of recommended (but not obligatory) prayers before or after some of the aforementioned five obligatory prayer sessions. These recommended prayer sessions typically include two to four prayer units. Another example is during the month of Ramadan in the Islamic calendar, when additional prayers may be offered after the night prayer. The additional prayers are in sets of two prayer units and typically, four to ten sets of these additional prayers are offered. Yet another example is the offering of the celebratory Eid prayers marking the end of Ramadan. Hereinafter, such prayer sessions that are outside of the five obligatory prayer sessions may be referred to as non-obligatory prayer sessions throughout this description.

In any event, regardless of the prayer session, each rakat or prayer unit in the prayer session follows the same series of postures: first standing with arms folded across the chest, then bowing with hands on knees (referred to as Raku), then brief standing with hands on the side, then prostrating two times with a brief sitting in between the two prostrations (each prostration is referred to as a Sajda). In the even prayer units or in the last prayer unit of the prayer session (regardless of whether the last prayer unit is an even or odd prayer unit), there is also a sitting step after the second prostration. Each of these postures within each prayer unit also involves specific recitations. Details of the prayer positions and postures in a prayer session are also described in U.S. Pat. No. 8,286,286 with reference to FIGS. 1-13, therein. U.S. Pat. No. 8,286,286 is incorporated herein by reference in its entirety.

While an individual is performing the prayer, the individual may forget which of the prayer units they are performing. If the individual realizes they may have not performed the correct number of prayer units for the prayer session they just completed, they either perform a subset of the prayer session all over again or instead perform a 'correction' prayer. Worse, if they didn't realize they made a mistake and do nothing about it, they may feel that the prayer session they just completed may not be recognized.

The present inventors have recognized that a solution may be provided to individuals performing the prayer sessions such that they can be assured that they performed the correct number of prayer units within each prayer session.

Accordingly, a non-limiting embodiment provides a method of tracking a prayer session of a device user and notifying the device user regarding prayer session activity, the method including receiving altitude information from an altimeter of the device while the device user is engaged in the prayer session, determining a prayer unit number or prayer position based on the received altitude information, and notifying the device user of the determined prayer unit number or prayer position.

The method may further include reading time information from a clock of the device, determining location information using GPS or cell towers, determining, based on the read time information and the determined location information, a type of prayer the device user is performing, corresponding time of day, and corresponding number of prayer units for the type of prayer, and notifying the user of the determined prayer unit number or prayer unit position based on the determined type of prayer.

The notifying may further include notifying the device user of the determined prayer unit number or prayer position using one of a visual notification, audio notification, and haptic notification.

The method may further include storing user prayer activity information for each prayer session of the user, and displaying the user prayer activity information of the prayer sessions based on a comparison with other users' prayer activity information.

In another non-limiting embodiment, the above-described method using the altimeter information may be implemented as an application stored in a non-transitory computer readable medium, and the method steps are executed as functions of the application.

Another non-limiting embodiment provides a method of tracking a prayer session of a device user and notifying the device user regarding prayer session activity, the method including receiving motion information from an accelerometer of the device while the device user is engaged in the prayer session, receiving position information from a gyroscope of the device while the device user is engaged in the prayer session, determining a prayer unit number or prayer position based on the received motion information and position information, and notifying the device user of the determined prayer unit number or prayer position.

The method may further include reading time information from a clock of the device, determining location information using GPS or cell towers, determining, based on the read time information and the determined location information, a type of prayer the device user is performing, corresponding time of day, and corresponding number of prayer units for the type of prayer, and notifying the user of the determined prayer unit number or prayer unit position based on the determined type of prayer.

The notifying may further include notifying the device user of the determined prayer unit number or prayer position using one of a visual notification, audio notification, and haptic notification.

The method may further include storing user prayer activity information for each prayer session of the user, and displaying the user prayer activity information of the prayer sessions based on a comparison with other users' prayer activity information.

In another non-limiting embodiment, the above-described method using the motion information and position information may be implemented as an application stored in a non-transitory computer readable medium, and the method steps are executed as functions of the application.

In yet another non-limiting embodiment, provided is a method of tracking a prayer session of a device user and notifying the device user regarding prayer session activity, the method including receiving motion information from an accelerometer of the device while the device user is engaged in the prayer session, receiving altitude information from an altimeter of the device while the device user is engaged in the prayer session, receiving position information from a gyroscope of the device while the device user is engaged in the prayer session, reading time information from a clock of the device, determining location information using GPS or cell towers, determining, based on the read time information and the determined location information, a type of prayer the device user is performing and corresponding number of prayer units for the type of prayer, determining a prayer unit number or prayer position based on one or more of the received motion information, altitude information, and position information; and notifying the device user of the determined prayer unit number or prayer position based on the determined type of prayer and corresponding number of prayer units for the type of prayer.

In another non-limiting embodiment, the above-described method using one or more of the motion information, altitude information, and position information may be implemented as an application stored in a non-transitory computer readable medium, and the method steps are executed as functions of the application.

BRIEF DESCRIPTION OF DRAWINGS

Color Drawings/Photographs

The patent or application file contains at least one drawing executed in color. Copies of this patent or patent application publication with color drawing(s) will be provided by the Office upon request and payment of the necessary fee.

DETAILED DESCRIPTION OF EXEMPLARY EMBODIMENTS

Figure 1:
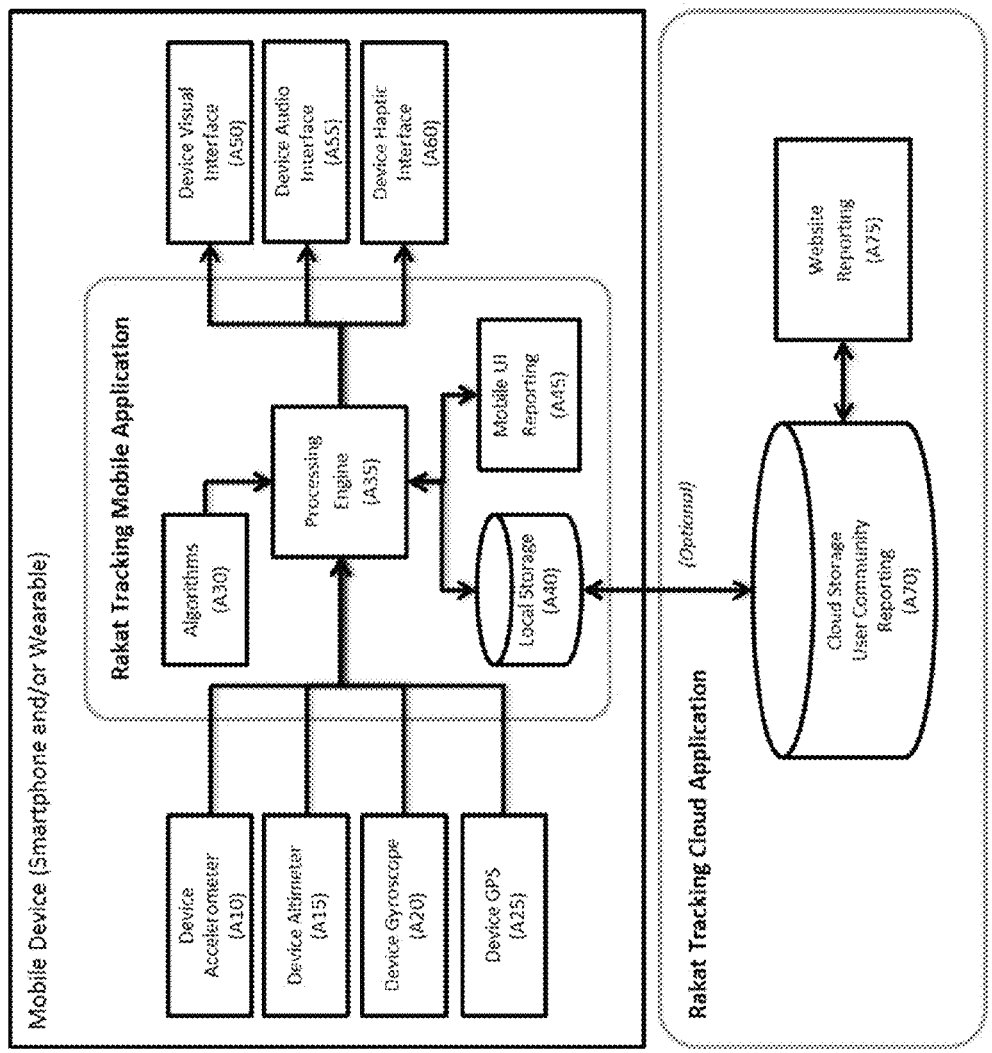
FIG. 1 is a view of a system for detecting prayer units in a prayer session according to a non-limiting embodiment.

All terms including descriptive or technical terms which are used herein should be construed as having their plain and ordinary meanings. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description. Thus, the terms used herein have to be defined based on the meaning of the terms together with the description throughout the specification.

Also, when a part "includes" or "comprises" an element, unless there is a particular description contrary thereto, the part may further include other elements, not excluding the other elements. In the following description, terms such as "unit" and "module" indicate a unit for processing at least one function or operation, wherein the unit and the block may be embodied as hardware or software or may be embodied by combining hardware and software.

One or more exemplary embodiments will now be described more fully with reference to the accompanying drawings. However, the one or more exemplary embodiments may be embodied in many different forms, and should not be construed as being limited to the exemplary embodiments set forth herein. Rather, these exemplary embodiments are provided so that this disclosure will be thorough and complete, and will fully convey the concept of the one or more exemplary embodiments to those of ordinary skill in the art. In the following description, well-known functions or constructions are not described in detail since they would obscure the one or more exemplar embodiments with unnecessary detail, and like reference numerals in the drawings denote like or similar elements throughout the specification.

It will be readily understood that the components of the present invention, as generally described and illustrated in the figures herein, may be arranged and designed in a wide variety of different configurations. Thus, the following more detailed description of the embodiments as represented in FIGS. 1-9B, is not intended to limit the scope of the invention, as claimed, but is merely representative of selected embodiments of the invention.

Referring now to FIGS. 1-9B, systems and methods for detecting prayer units while an individual is engaged in a prayer session will be described.

In one embodiment, a mobile application is provided for a device such as a smartphone (e.g., Apple iPhones, Android-based smartphones, etc.) and/or a wearable device (e.g., Apple Watch, Samsung wearable technology, Pebble, FitBit, Pendent, Clip-On, etc.). For example, the mobile application can work on both the smartphone and wearable device or work on only one of the smartphone and wearable device. The mobile application would allow users to keep track of the prayer units they are performing and/or keep track of prayer postures within each prayer unit (e.g., standing, bowing, sitting, or prostrating—in other words, any posture in the above-noted series of postures in a prayer unit) and alert the user of the prayer unit count and/or prayer postures via visual notifications (icons, flashing lights, graphics, colors, etc.), audio notifications (beeps, music, dialogue, etc.), and haptic notifications (pulse, vibrate, etc.) for the purpose of correctly performing prayers and/or tracking and reporting on prayers. Furthermore, the user can disable the alerting altogether (e.g., for the purpose of not being disturbed during the prayer), so that they can review their "tracking" of their prayer positions and sequence after their prayer to see if their prayer was performed properly or if they should repeat their prayer.

The mobile application utilizes one or more of the device's accelerometer, altimeter, gyroscope, and GPS to track and analyze the user's motion, altitude, position, and location (assuming the user is carrying or wearing the device) in order to determine the prayer unit count and/or prayer position/posture. Prayer position and prayer posture may be interchangeably used throughout this disclosure. The mobile application's algorithms gather data regarding accelerometer, altimeter, gyroscope, and location and assess the data individually or in combination with each other to determine the user's current sequence in the prayer session and predict the next action in the sequence. Additionally, depending on the device capabilities, only one data stream, such as the user's altitude information, could be used to determine the prayer unit count and/or prayer position without collecting or analyzing the other data streams (motion, position, location). Moreover, the algorithms may look at the user's historic data points for all the user's previous prayer sessions (or for all the user's previous prayer sessions for the particular prayer being offered) along with current data points to determine the User's current sequence and/or position and predict the next action in the sequence and/or to present the user's prayer activity information. Furthermore, the algorithms can alert the user of their current sequence without predicting the next action in the sequence.

The mobile application can be manually started by the user prior to a prayer session. In another embodiment, the application can self-activate when it detects the user has started the prayer session by monitoring the data points against a prayer sequence pattern of data points. In yet another embodiment, the application can self-activate when it detects the user has started the prayer session by monitoring the data points against a prayer sequence pattern of data points and also based on the time of day. The self-activation mode requires the mobile application to run in the background continuously upon device startup or when manually started by user. Furthermore, at any time, the user can restart/reset the prayer unit count manually to zero or the prayer position to an initial state if desired both in the manual start mode or the self-activate mode.

The mobile application utilizes the device's GPS and system clock to determine the user's location and time of day in order to determine which of the five prayers the user will most likely be conducting. Further, the application can recommend to the user which of the five prayers and number of prayer units to perform. The user can also manually enter their location and/or which prayer they will be conducting.

The mobile application has a calibration sequence which allows the user, if they desire, to standardize/tune the application's algorithms to their unique prayer positions in order to increase the accuracy of the prayer position identification and notification. The calibration sequence monitors and records the accelerometer, altimeter, and gyroscope data points for the user during a practice prayer sequence and uses this recorded information as a baseline to compare against to determine prayer positions and prayer units. For example, in order to calibrate the application, the user can direct the application to activate a calibration mode in which the user can perform a practice prayer session prior to performing an actual prayer session. This way, during the practice prayer session, the application can detect the user's tendencies in a prayer unit and more particularly within each prayer position and transitions between prayer positions. For example, the application can determine the average time a user spends in the standing position, bowing position, prostrating position, etc. Additionally, the calibration sequence can utilize application community user data as a baseline to compare against to determine prayer positions and prayer units. Both of these calibration methods are a form of machine learning in order to provide more accurate prayers positions identification and notification. This calibration sequence is optional for the user. The application community user data is described in more detail below.

The mobile application employs visual notifications (user configurable) in addition to audio and haptic notifications to alert the user of the current sequence of their prayer sequence and/or the predicted next sequence. The visual notifications can consist of images, avatars, logos, characters, numbers, and/or alphanumeric displayed on the device screen (smartphone, wearable technology, etc.) to indicate prayer sequence steps. In addition flashing lights and various screen colors can also be utilized as notifications. For example, a certain color, such as red, might be use to designate the first prayer unit while another color, such as yellow, might be used to designate the second prayer unit. In another example, certain images or symbols, such as a triangle, might be use to designate the first prayer unit while another image or symbol, such as a square, might be used to designate the second prayer unit. The visual notifications can occur on both the smartphone device and wearable device or just on a single device, either the smartphone device or the wearable device.

The mobile application employs audio notifications (user configurable) in addition to visual and haptic notifications to alert the user of the current sequence (e.g., prayer unit or prayer position) of their prayer sequence and/or the predicted next sequence. The audio notifications can consist of beeps, music, and/or human voice commands from the device (smartphone, wearable, etc.) to indicate prayer sequence steps. The audio notifications can occur on both the smartphone device and wearable device or just on a single device, either the smartphone device or the wearable device.

The mobile application employs haptic notifications (which may be user configurable) in addition to visual and audio notifications to alert the user of the current sequence of their prayer sequence and/or the predicted next sequence. The haptic notifications can consist of pulses and/or vibrations from the device (smartphone, wearable, etc.) to indicate prayer sequence steps. The haptic notifications can occur on both the smartphone device and wearable device or just on a single device, either the smartphone device or the wearable device.

The mobile application allows users to disable their notifications (audio, visual and haptic) altogether and the user can review their prayer unit count and prayer position details after the prayer session if they prefer not being bothered during the prayer. Of course, even if the notifications are enabled, the user could still review their prayer unit count and prayer position details after the prayer session.

The mobile application enables users to track their total, average, and other metrics for prayer units and prayer postures/positions performed for each of the five obligatory prayer sessions per day or for non-obligatory prayers, for all prayer units performed and all prayer positions the user engaged in per each of the five prayer sessions, for all prayer units performed per day of the week, for all prayer units performed per day/week/month/quarter/year both in Julian and Hijra (Islamic) calendar years and lifetime Additionally, the user can share/post their total/average prayer unit and prayer position metrics with another user of the prayer unit counting and analysis mobile application, with a group of members, and/or to the entire user community (i.e., all users of the mobile application). Furthermore, users can compare their prayer unit totals either by prayer, day, day of week, week, month, etc. with the user community benchmarks (aggregated totals and averages across entire mobile application user community). Additionally, users can keep a running count of prayer units they have performed since installing the mobile application providing them with per lifetime prayer units tracking and reporting. Lastly, based on their performance metrics, users can receive digital badges, rewards, and other forms of recognition (Gamify) for their prayer unit metrics.

The mobile application also allows users to track their prayer positions/postures and provides analytics (prayer analytics) on how they are performing their prayers based on which of the five obligatory prayers or non-obligatory prayers or all prayers across a certain day, time, and/or period. For example, this allows users to review if they are taking more time in between the two prostrations during the dawn prayer versus the noon or afternoon prayers, or if the user's second prayer units frequently tends to be quicker than their first prayer unit (i.e., the time it takes the user to complete the second prayer unit tends to be less than the time it takes the user to complete the first prayer unit). By providing these trends to the user, in addition to providing visibility into the user's praying habits, the user can decide if they want to make certain changes to their prayers (for quality optimization purposes). Moreover, a user's data can be compared with community data to identify areas of optimization. For example, information may be provided to the user based on the user's data and the community data that the user was in the $95^{th}$ percentile of performing his afternoon prayer on time.

Users are able to post their prayer session metrics and digital badges, rewards, and other recognitions to mobile and cloud application as well as other social media applications (Facebook, Twitter, Instagram, etc.).

In light of the above functionality, configuration, and capabilities of the disclosed mobile application, the mobile application can easily, accurately, and automatically count a user's prayer units when the user is performing prayers and notify the user of the current prayer unit count and/or prayer position in a non-obtrusive manner in order to perform prayers correctly.

Users can track and share (if desired) their prayer session metrics for a certain time period or prayer session. Users can also monitor their prayers session activity and make adjustments for quality optimization purposes. Users can also utilize the prayer session metrics to encourage a certain behavior. For example, users can be encouraged to make corrections in their prayer session, be encouraged to pray more regularly, and also inspire others to pray.

FIG. 1 is a view of a system for detecting prayer units in a prayer session according to a non-limiting embodiment.

In FIG. 1, device accelerometer A10 is a device (smartphone and/or wearable) component that tracks, records, and reports acceleration and speed data of the device (xyz-axis acceleration and xyz-axis rotation rate). The device altimeter A15 is a mobile device (smartphone and/or wearable) component that tracks, records and reports altitude data of the device. The device gyroscope A20 is a mobile device (smartphone and/or wearable) component that tracks, records and reports alignment orientation data of the device relative to the earth's gravity (roll, pitch, yaw, and xyz-gravity). The device global positioning system (GPS) A25 is a device (smartphone and/or wearable) component that tracks, records, and reports location data of the device.

The algorithms A30 are procedures to determine rakat (prayer unit) count and prayer position based on data collected from the device accelerometer A10, device altimeter A15, device gyroscope A20, and/or device GPS A25. Examples of algorithms A30 will be described in further detail with reference to FIGS. 2-3 and 4A-9B. The processing engine A35 is a hardware and/or software processor that determines the rakat (prayer unit) count and prayer position by executing the algorithms A30 using the collected data as input. The processing engine A35 also determines calculations for all reporting requirements and determines the notifications to be made and the timing of those notifications.

The local storage A40 is a data store (e.g., physical memory) on the device (e.g., smartphone and/or wearable) that stores the data collected by the device sensors (accelerometer A10, altimeter A15, gyroscope A20, and GPS A25) and the data/metrics calculated by the processing engine A35 as a result of executing the algorithm(s) A30. The local storage A40 also stores user configuration data. The mobile user interface (UI) reporting module A45 is an application display module of the mobile application for generating the type and format of information (e.g. prayer activity information) to be presented from among the collected and calculated data/metrics mentioned above.

The device visual interface A50 is a mobile device (smartphone and/or wearable) component that presents information (e.g., prayer activity information) to the user via visual elements (graphs, texts, diagrams, etc.) as determined by the processing engine A35 and the mobile UI reporting module A45. The device audio interface A55 is a mobile device (smartphone and/or wearable) component that presents information (e.g., prayer activity information) to the user via auditory elements (audible tones, voice, music, etc.) as determined by the processing engine A35 and the mobile UI reporting module A45. The device haptic interface A60 is a mobile device (smartphone and/or wearable) component that presents information (e.g., prayer activity information) to the user via vibratory elements (vibrations, etc.) as determined by the processing engine A35 and the mobile UI reporting module A45.

The cloud storage user community reporting database is a data store on a central server that stores data and metrics collected by the device sensors (accelerometer A10, altimeter A15, gyroscope A20, and GPS A25) and the data/metrics determined by the processing engine A35 as a result of executing the algorithm(s) A30 across the entire user community (i.e., all users executing the mobile application for prayer tracking). The website reporting module A75 is an application display of collected and calculated data/metrics across the entire user community.

To be able to determine the prayer unit count and/or the prayer position or to predict and recommend the next step, multiple algorithms may be used either individually or in combination to increase accuracy. The algorithm(s) used will depend on the data that is available from the device.

Figure 2:
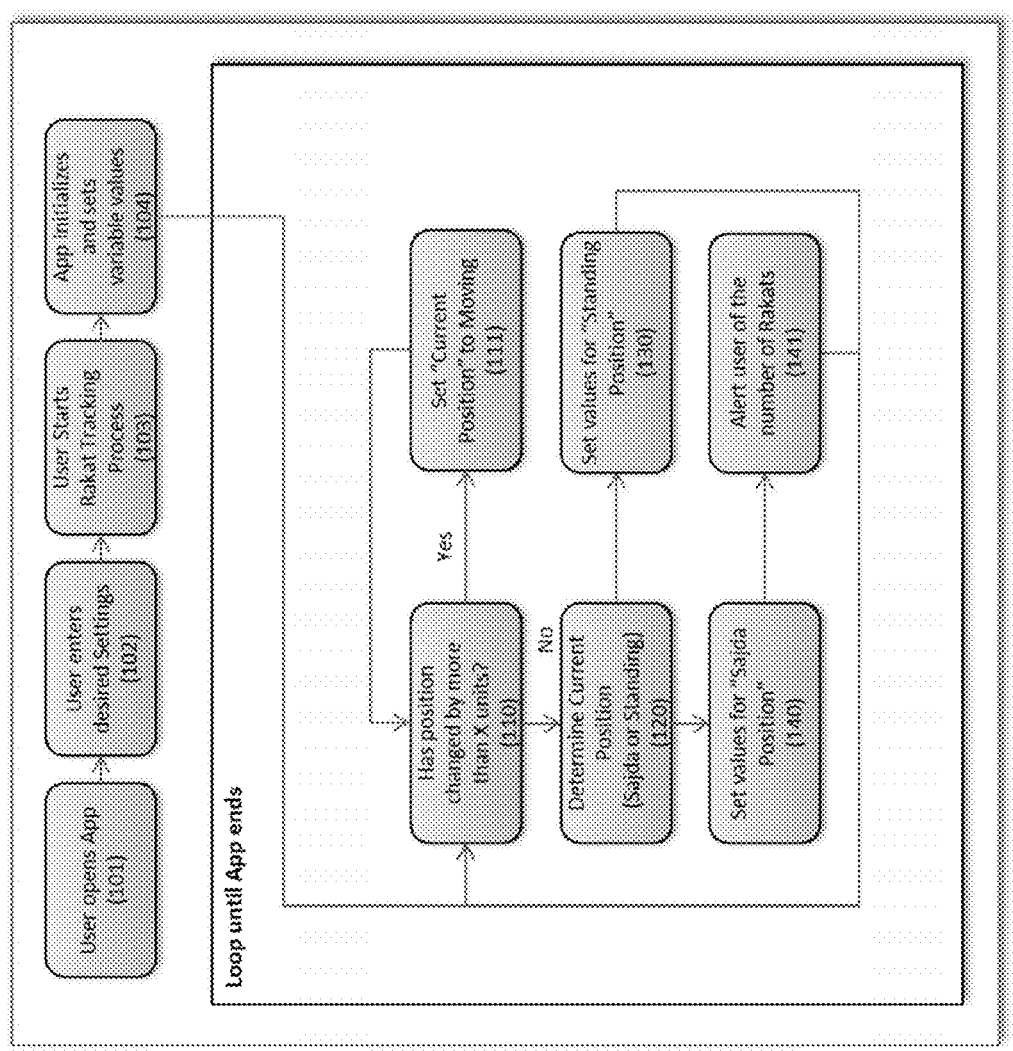
FIG. 2 is a flowchart illustrating the implementation of the method for detecting prayer units using output from an altimeter according to a non-limiting embodiment.

FIG. 2 is a flowchart illustrating the implementation of the method for detecting prayer units using output from an altimeter according to a non-limiting embodiment.

The method in FIG. 2 is an altimeter based algorithm, executed in the application running, e.g., on a smartphone. The altimeter based algorithm analyzes relative position and altitude using barometric pressure sensors.

As shown in FIG. 2, in the altimeter based algorithm, a user is allowed to set a "Relative Difference" setting(s) that the mobile application will use to assess patterns unique to the users. These settings might be adjusted as needed for fine tuning the accuracy of the application. For the altimeter based algorithm with the smartphone or other mobile device in the pocket while the user is engaged in the prayer session, a proper height difference should be set between a person's standing position and the prostration and/or sitting positions. If the phone were in a user's pocket, we would need to estimate the distance between height of the pocket when standing versus. when sitting, which is the relative distance in this scenario. The user should be able to tune this "Relative Distance" value to make the calculations more accurate. For example, the user may want to increase or decrease the distance. In this exemplary embodiment, 20 inches is set as the default, which may work for some people, but may not be ideal for others (in which case they can tune the value). In the wrist-based mobile devices such as the Apple watch, the "Relative Setting(s)" may be more nuanced which may include the distance between altitude from various positions (e.g., Takbir (raising of hands), standing, Raku (bowing), sitting).

In FIG. 2, the application will follow this overview of the algorithm below for the prayer tracking process (which involves tracking at least the rakats (prayer units) and the prayer positions within each rakat (prayer unit)).

1) The altimeter based algorithm begins with step 101 where the user starts the application for prayer tracking.
2) Step 102 allows the user to set desired setting(s) (such as "Relative Difference") that the application will use to assess patterns unique to the users. These settings might be adjusted as needed for fine tuning the accuracy of the application.
3) Once the user indicates to the application in step 103 (e.g., by making an appropriate selection in the application) that the application should start the prayer tracking process (e.g., right before the user begins a prayer session), the application will follow the following overview of an exemplary algorithm A30 executed on the processing engine A35 using data collected by the device altimeter A15.
  a) Capture "Current Altitude" settings multiple times a second (103).
  b) Set Variables (104):
    i) Determine the current altitude of the user in 'Standing' position. Set the value as "Standing Altitude".
    ii) Set the "Current Position" to Standing.
    iii) Set the "Prostration Altitude" to Standing Altitude—Relative Difference.
    iv) Set Prostration_Num=0
    v) Set Prayer_Unit_Num=1
  c) Compare the "Current Altitude" to prior recorded altitude (110).
    i) Loop
      (1) If the altitude changes by more than X units (Variance setting) from Prior position (110), then
        (a) Set the "Current Position" to "Moving" (111)
        (b) If the altitude is within range of X units variance for the last 5 measurements, determine if the altitude is within the Standing Altitude or the Prostration Altitude (120).
          (i) If in Standing Range (130):
            1. Set "Current Position" to "Standing"
            2. Update mobile UI A45 with Prayer_Unit_Num value
          (ii) If in Prostration Range (140):
            1. If "Current Position" is not "Prostration"
              a. Set Current Position to "Prostration"

b. Increment Prostration_Num by +1
c. Set Prayer_Unit_Num to ROUND_DOWN (Prostration_Num)+1
d. If Prostration_Num is even number, Alert user of the Prayer_Unit_Num (141).
  2. If position is "Prostration", no action.

Figure 3:
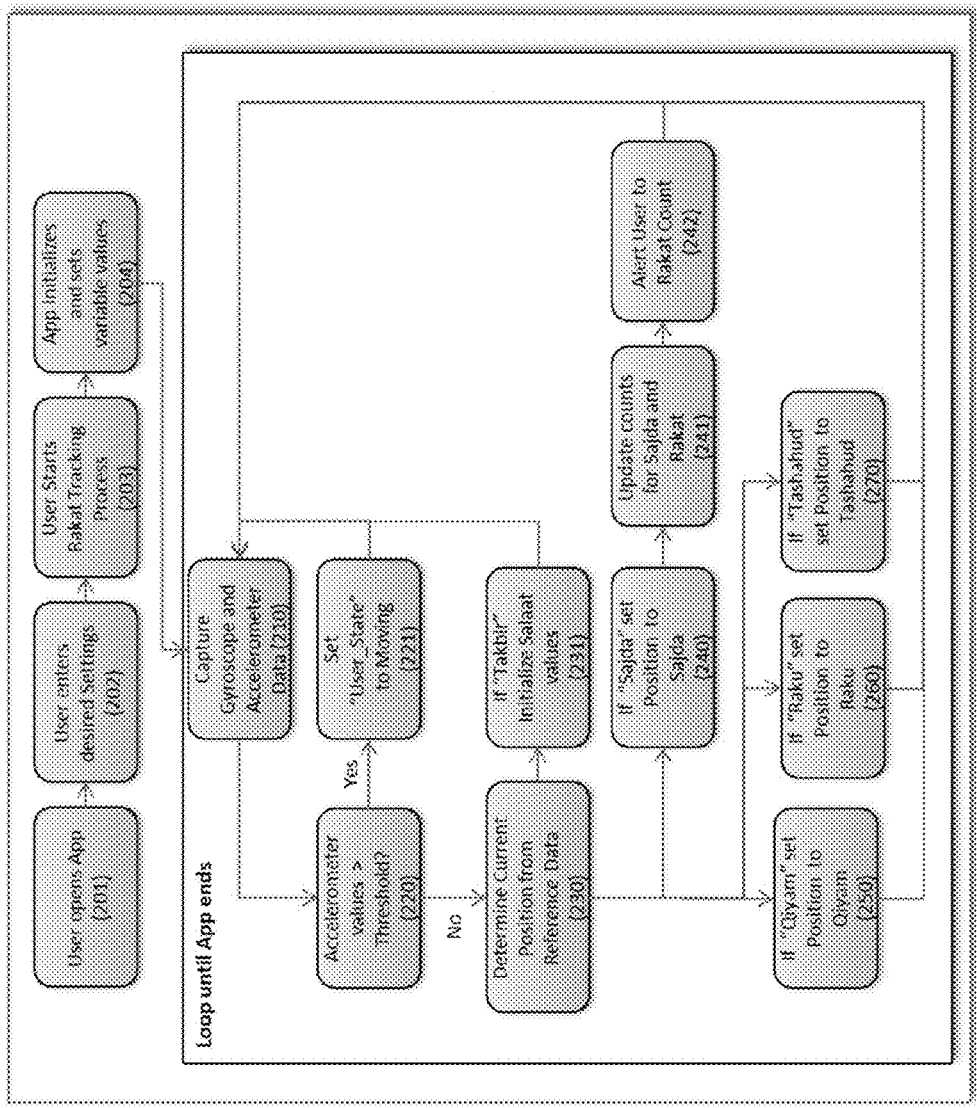
FIG. 3 is a flowchart illustrating the implementation of the method for detecting prayer units using output from an accelerometer and a gyroscope according to another non-limiting embodiment.

FIG. 3 is a flowchart illustrating the implementation of the method for detecting prayer units using output from an accelerometer and a gyroscope according to another non-limiting embodiment.

The method in FIG. 3 is a gyroscope and accelerometer based algorithm that analyzes user position using device's 3-axis position and 3-axis acceleration sensors.

As shown in FIG. 3, in the gyroscope and accelerometer based algorithm, a user is allowed to set a calibrate setting(s) that the application will use to assess patterns unique to the users. These settings might be adjusted as needed for fine tuning the accuracy of the application. For example, the user can define or make the application aware of the following: Multiple Takbirs (raising of hands multiple times): Some individuals do multiple Takbir's during the prayer session, and the application should know this to properly identify a prayer unit (rakat) number.

Certain sects of Muslims do not put their hands on their waist when they stand, while others do so this can be defined.

Some people with knee or joint issues cannot sit properly when they are in the prayer session, and the application can account for this if it is made aware of such issues.

Men and women hold their hands at different positions while standing, and the application can make appropriate adjustments.

In essence, the more data unique to the user the application can capture or be made aware of, the more detailed the algorithm can be, especially by adjusting the reference positions and movement patterns dynamically for each person.

In FIG. 3, the application will follow the overview of the algorithm below for the prayer tracking process (which involves tracking at least the rakats (prayer units) and the prayer positions within each rakat (prayer unit)).
1) The gyroscope and accelerometer based algorithm begins with step 201 where the user starts the application for prayer tracking.
2) Step 202 allows the user to set desired settings that the application will use to assess patterns unique to the users. These settings might be adjusted as needed for fine tuning the accuracy of the application.
3) Once the user indicates to the application in step 203 (e.g., by making an appropriate selection in the application) that the application should start the prayer tracking process (203) (e.g., right before the user begins a prayer session), the application will follow the following overview of an exemplary algorithm A30 executed on the processing engine A35 using data collected by the device accelerometer A10 and device gyroscope A20.
  a) Load gyroscope and accelerometer position values for prayer positions for raising hands to head (Takbir), standing (Qiyam), bowing (Raku), prostration (Sajda), and sitting between prostrations (Tashahud). Each position could have multiple possible setting to accommodate the different ways in which a user can wear a device (left/right hand, inside/outside of wrist etc.) (204).
  b) Capture gyroscope and accelerometer values multiple times a second (210) using the device gyroscope A20 and device accelerometer A10.
  c) If Acceleration_Values>0.03 (220), then
    i) Set User_State as "Moving" (221)
  d) If "Acceleration_Values"<=0.03, Determine current position from Reference Data (230)
    i) If position values match those of Takbir (231), Set Variables:
      (1) If Position not equal to "Takbir"
        (a) If Takbir_Count=0,
          (i) Set Sajda_Num=0
          (ii) Set Prayer_Unit_Started_Num=1+(RoundUp (Sajda/2))
          (iii) Set Prayer_Unit_Finished_Num=RoundUp (Sajda/2)
        (b) Increment Takbir_Count by 1
        (c) Set Position="Takbir"
    ii) If position values match those of Qiyam (250), Set Variables:
      (1) Set Position="Qiyam"
    iii) If position values match those of Raku (260), Set Variables:
      (1) Set Position="Raku"
    iv) If position values match those of Sajda (240), Set Variables:
      (1) If Postion is not equal to "Sajda"
        (a) Set Position="Sajda"
        (b) Set Sajda_Num=Sajda_Num+1
        (c) Set Prayer_Unit_Started_Num=1+(RoundDown (Sajda_Num/2))
        (d) Set Prayer_Unit_Finished_Num=RoundDown (Sajda_Num/2)
        (e) If Sajda_Num is even number, alert the user with a count number of "Prayer_Unit_Started_Num"
    v) If position values match those of Tashahud (270), Set Variables:
      (1) Set Position="Tashahud"

The mobile application embodiments disclosed above with respect to FIG. 2 or 3 or other such embodiments may utilize the device GPS A25 and a system clock to determine the user's location and time of day in order to determine which of the five obligatory prayers or a non-obligatory prayer the user will most likely be conducting. Further, the application can recommend to the user which of the five obligatory prayers or non-obligatory prayer along with the number of prayer units to perform. The user can also manually enter their location and/or which prayer they will be conducting.

FIGS. 4A-9B illustrate the present inventors' work in identifying thresholds for determining prayer units and prayer positions while a user is engaged in a prayer session.

Figure 4A:
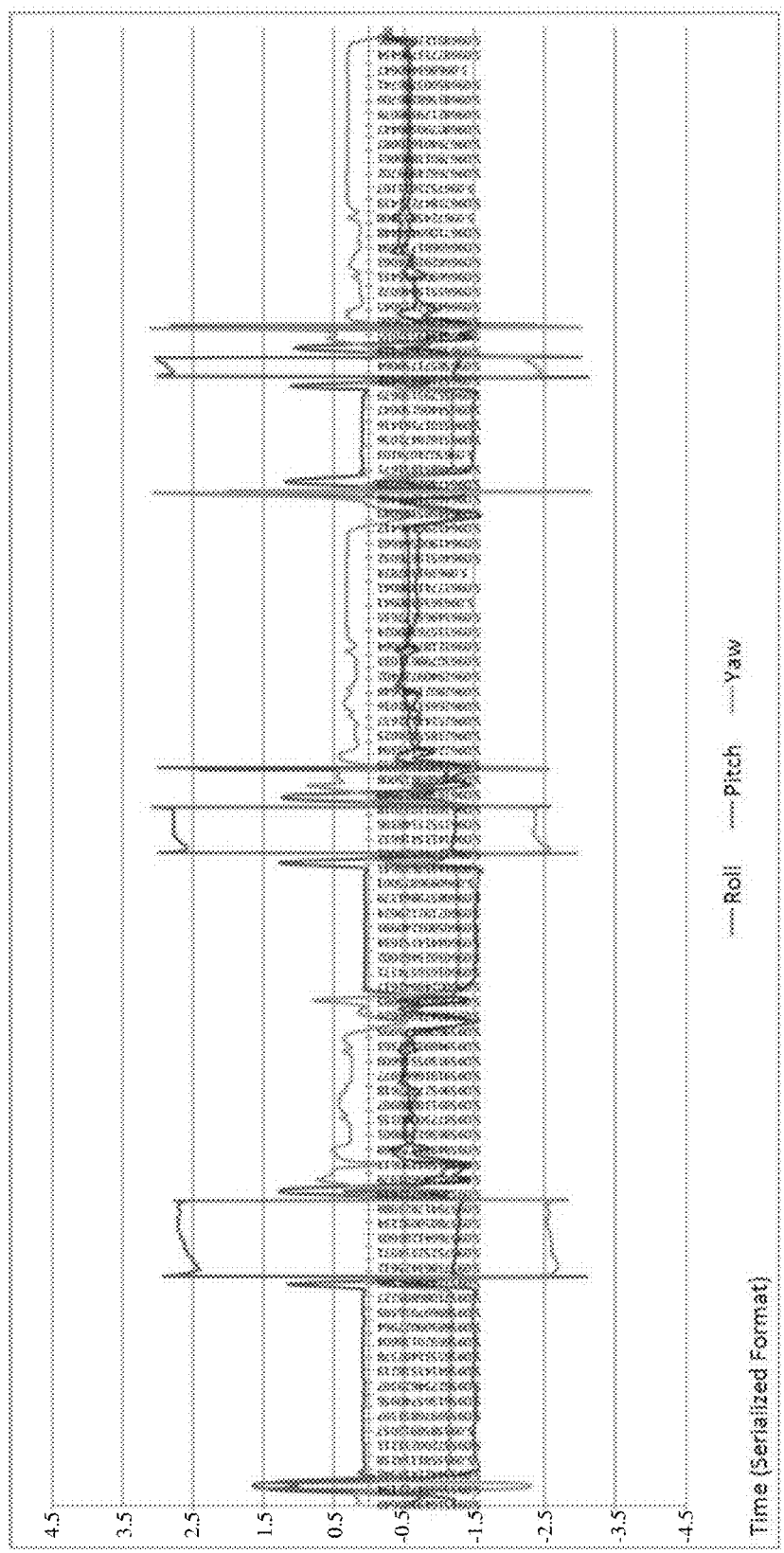
FIG. 4A is a graph which shows collected roll, pitch, and yaw data from a device's gyroscope to show positional orientation of the device during an exemplary prayer session including three prayer units.

FIG. 4A is a graph which shows collected roll, pitch, and yaw data from a device's gyroscope to show positional orientation of the device during an exemplary prayer session including three prayer units.

Figure 4B:
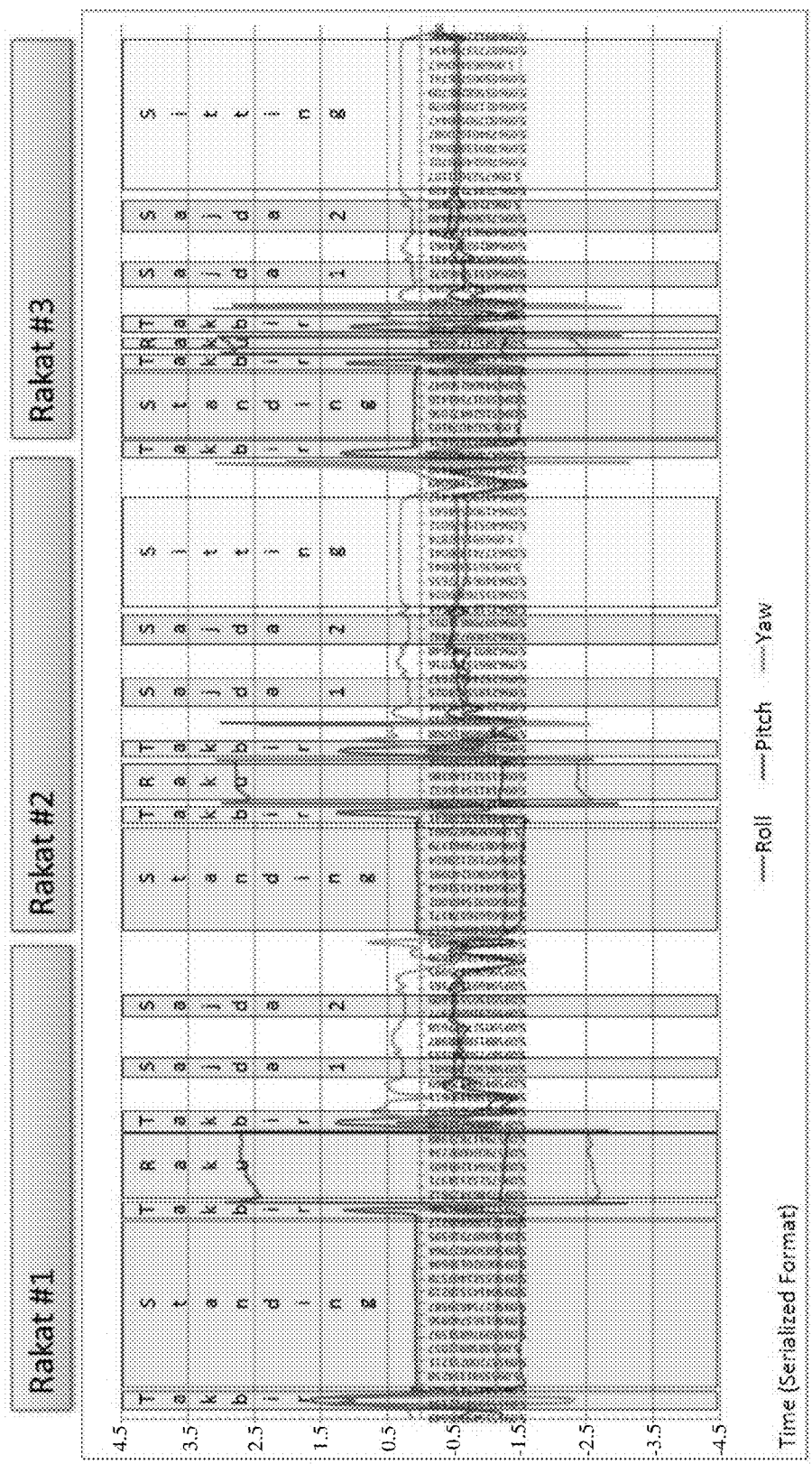
FIG. 4B is a graph which shows a coded overlay on top of the data from FIG. 4A to show the breakdown of the positional orientation of the device corresponding to the specific posture of the user within each prayer unit of the three prayer units in the exemplary prayer session.

FIG. 4B is a graph which shows a coded overlay on top of the data from FIG. 4A to show the breakdown of the positional orientation of the device corresponding to the specific posture of the user within each prayer unit of the three prayer units in the exemplary prayer session.

Figure 5A:
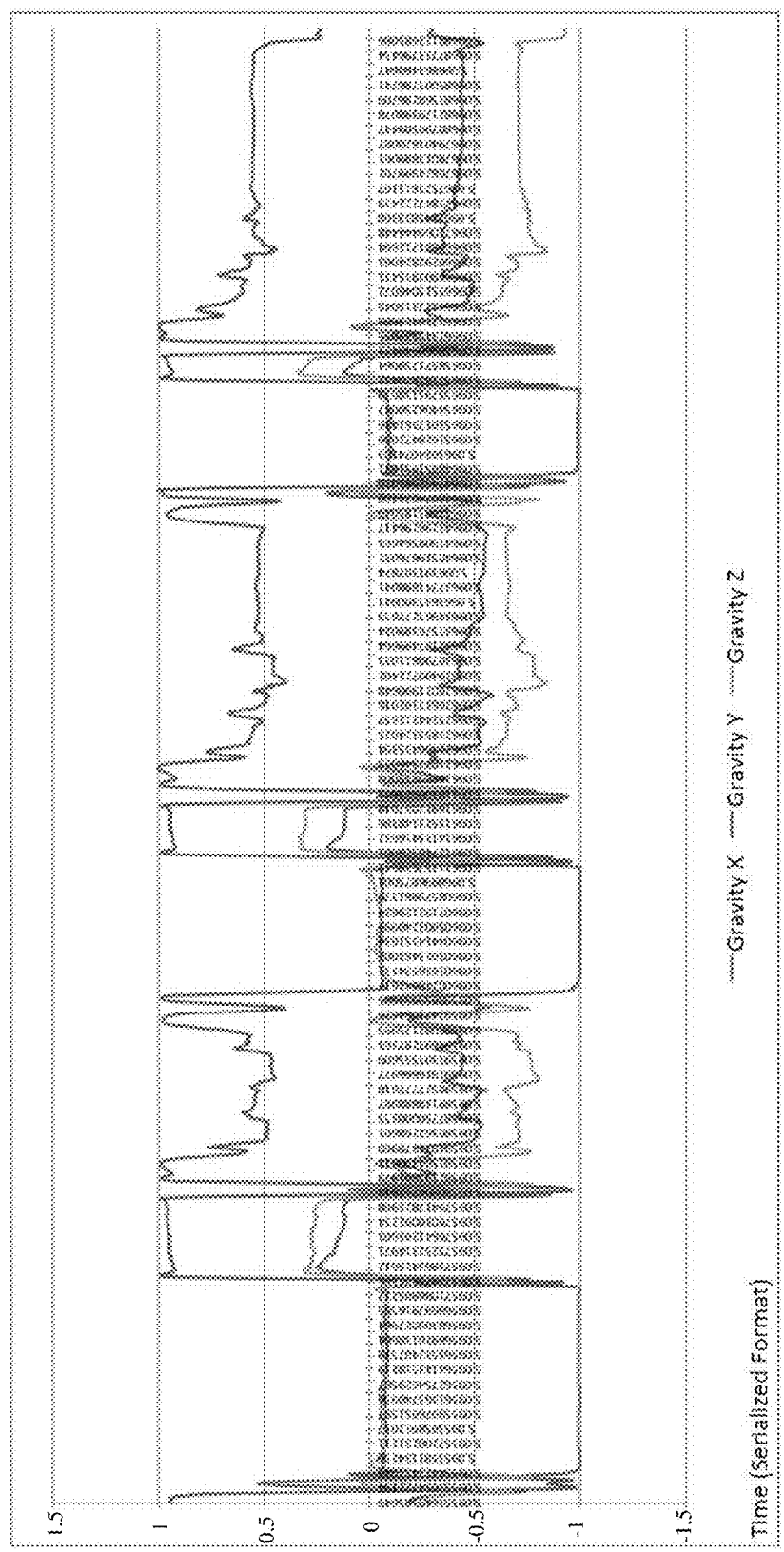
FIG. 5A is a graph which shows collected XYZ gravity data from a device's gyroscope to show positional orientation of the device during an exemplary prayer session including three prayer units.

FIG. 5A is a graph which shows collected XYZ gravity data from a device's gyroscope to show positional orientation of the device during an exemplary prayer session including three prayer units.

Figure 5B:
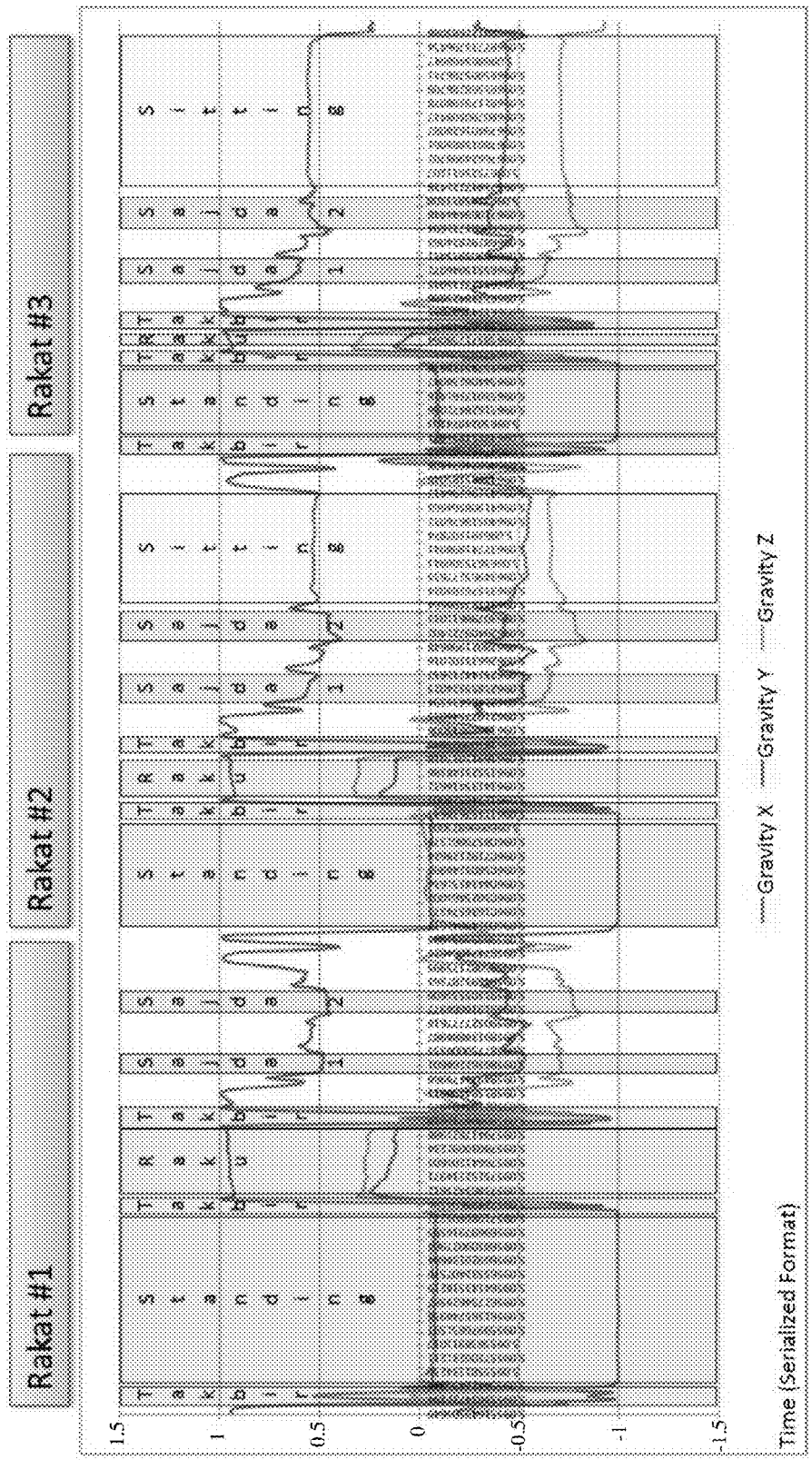
FIG. 5B is a graph which shows a coded overlay on top of the data from FIG. 5A to show the breakdown of the positional orientation of the device corresponding to the specific posture of the user within each prayer unit of the three prayer units in the exemplary prayer session.

FIG. 5B is a graph which shows a coded overlay on top of the data from FIG. 5A to show the breakdown of the positional orientation of the device corresponding to the specific posture of the user within each prayer unit of the three prayer units in the exemplary prayer session.

Figure 6A:
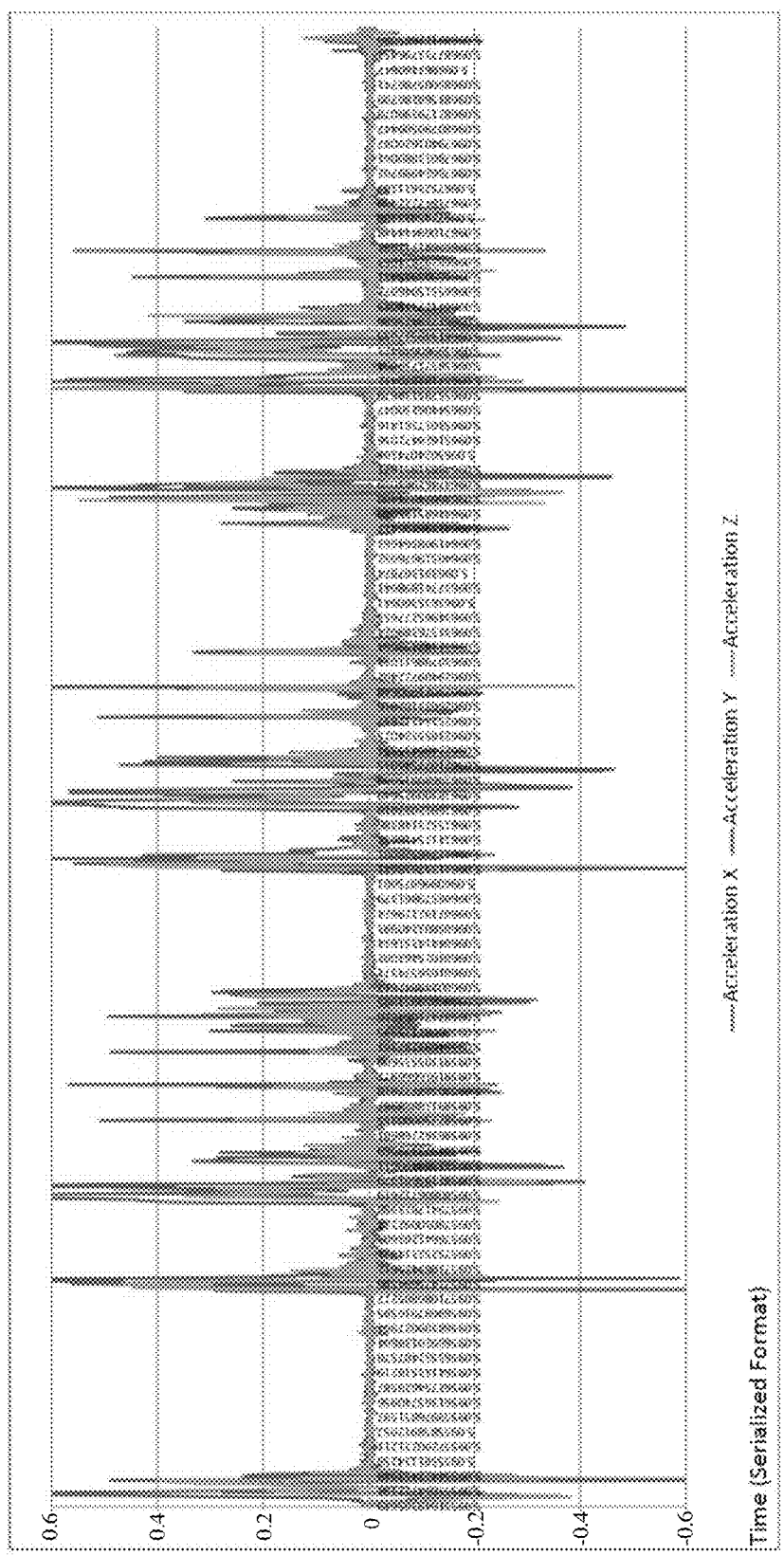
FIG. 6A is a graph which shows collected XYZ acceleration data from a device's accelerometer to show the movement (and lack thereof) of the device when transitioning from one posture of a prayer unit to another and transitioning between prayer units during an exemplary prayer session including three prayer units.

FIG. 6A is a graph which shows collected XYZ acceleration data from a device's accelerometer to show the movement (and lack thereof) of the device when transitioning from one posture of a prayer unit to another and transitioning between prayer units during an exemplary prayer session including three prayer units.

Figure 6B:
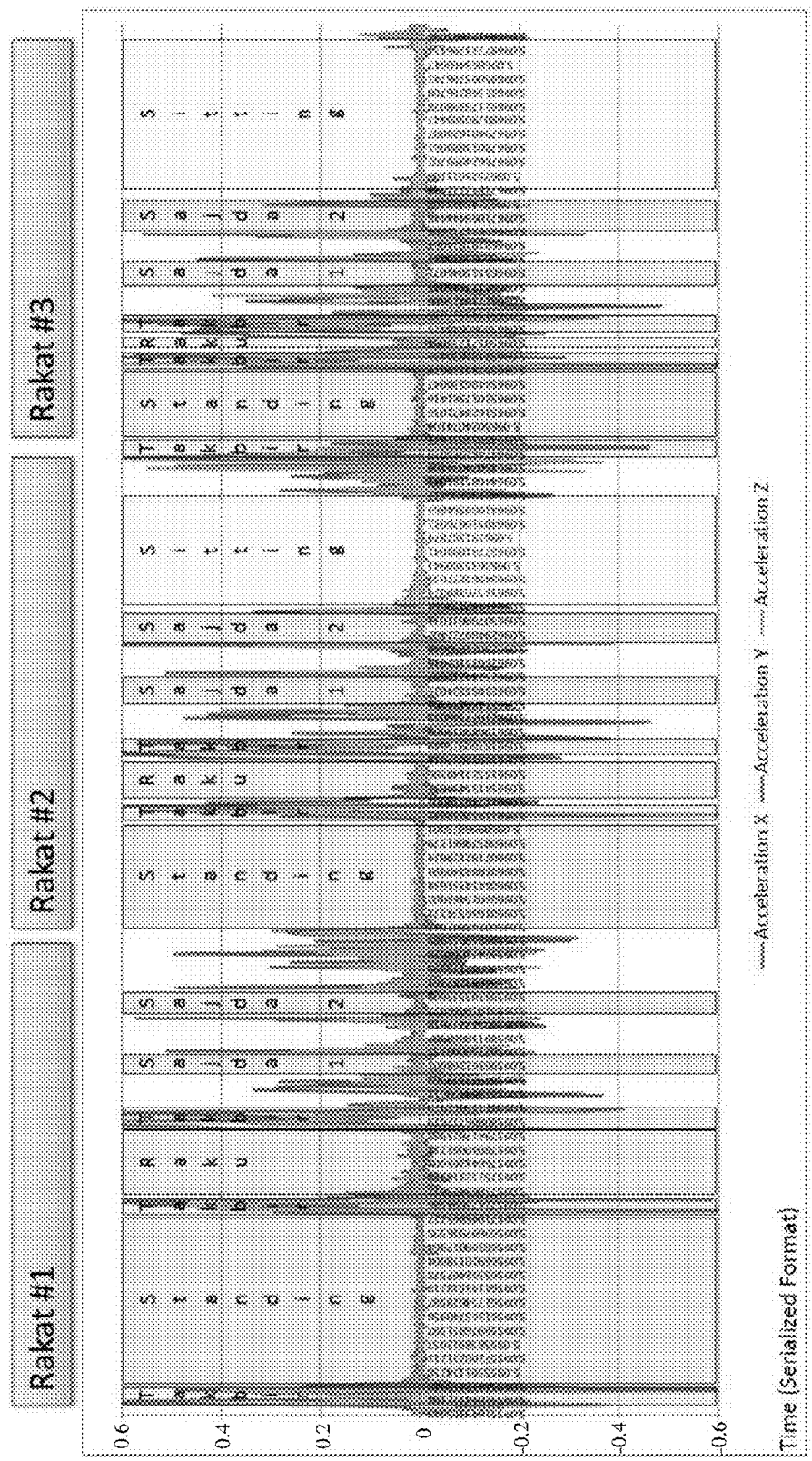
FIG. 6B is a graph which shows a coded overlay on top of the data from FIG. 6A to show the breakdown of the movement of the device corresponding to the user transitioning from one posture of a prayer unit to another and transitioning between prayer units in the exemplary prayer session.

FIG. 6B is a graph which shows a coded overlay on top of the data from FIG. 6A to show the breakdown of the movement of the device corresponding to the user transitioning from one posture of a prayer unit to another and transitioning between prayer units in the exemplary prayer session.

Figure 7A:
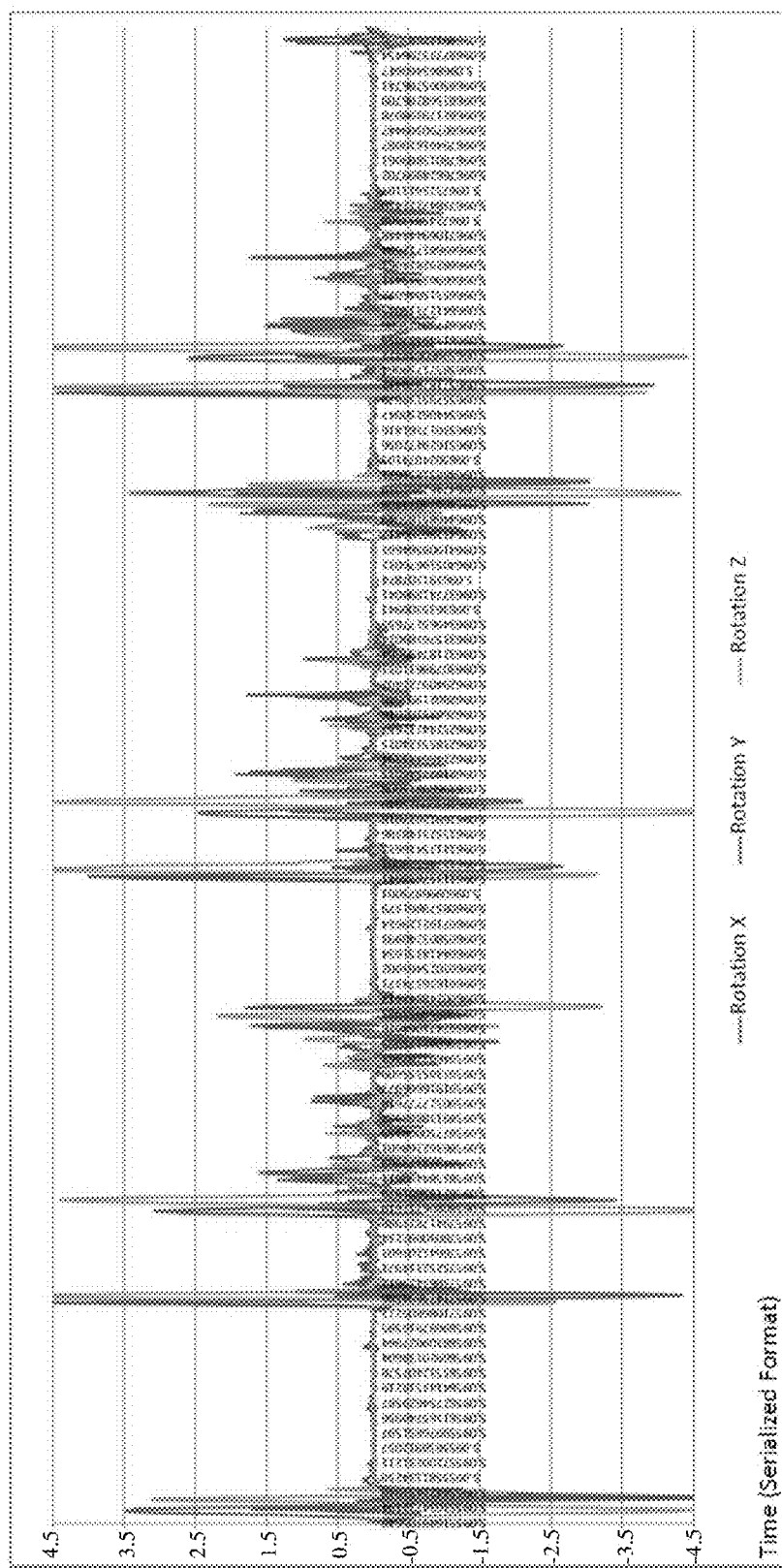
FIG. 7A is a graph which shows collected XYZ rotation data from a device's accelerometer to show the movement (and lack thereof) of the device when transitioning from one posture of a prayer unit to another and transitioning between prayer units during an exemplary prayer session including three prayer units.

FIG. 7A is a graph which shows collected XYZ rotation data from a device's accelerometer to show the movement (and lack thereof) of the device when transitioning from one posture of a prayer unit to another and transitioning between prayer units during an exemplary prayer session including three prayer units.

Figure 7B:
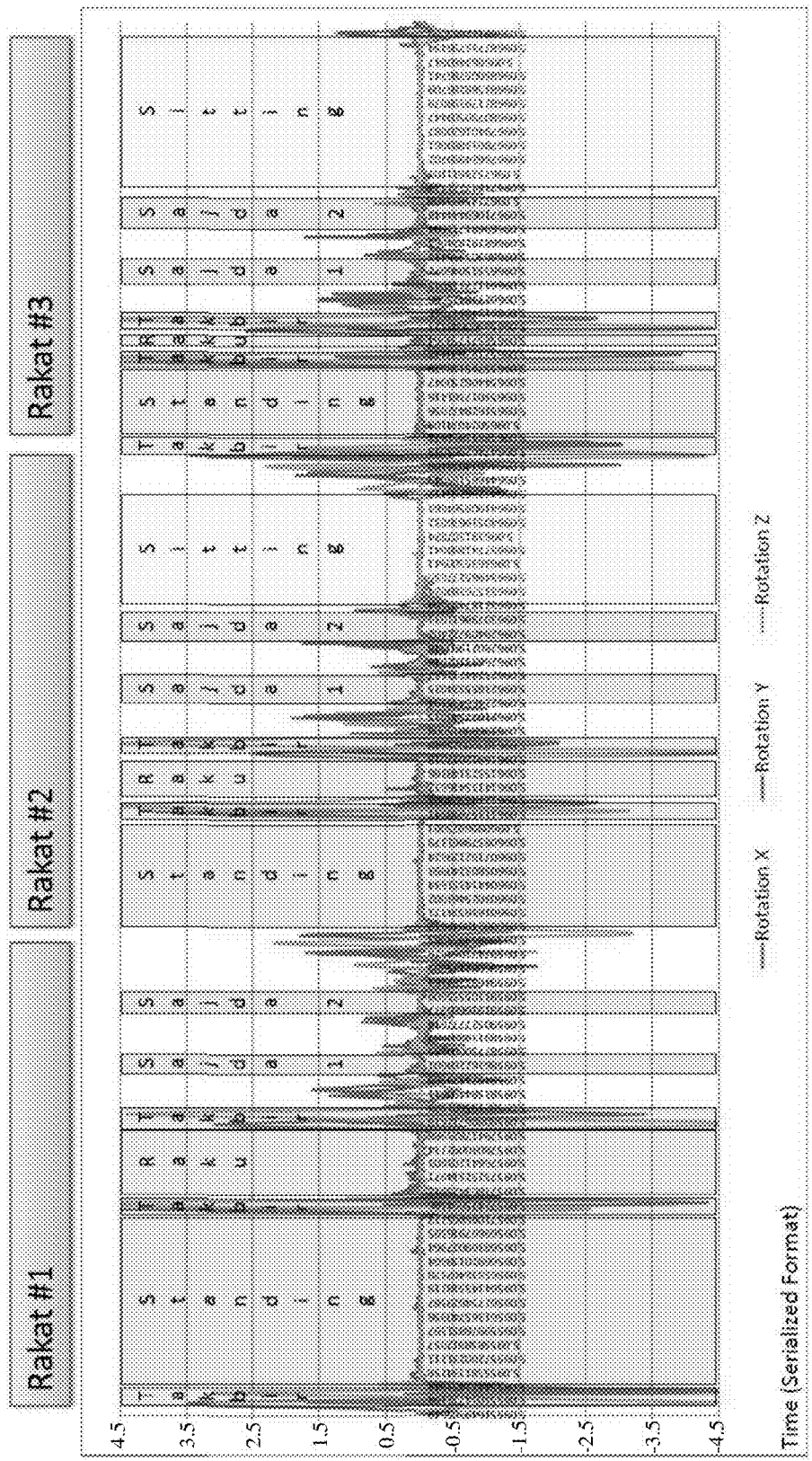
FIG. 7B is a graph which shows a coded overlay on top of the data from FIG. 7A to show the breakdown of the movement of the device corresponding to the user transitioning from one posture of a prayer unit to another and transitioning between prayer units in the exemplary prayer session.

FIG. 7B is a graph which shows a coded overlay on top of the data from FIG. 7A to show the breakdown of the movement of the device corresponding to the user transitioning from one posture of a prayer unit to another and transitioning between prayer units in the exemplary prayer session.

Figure 8A:
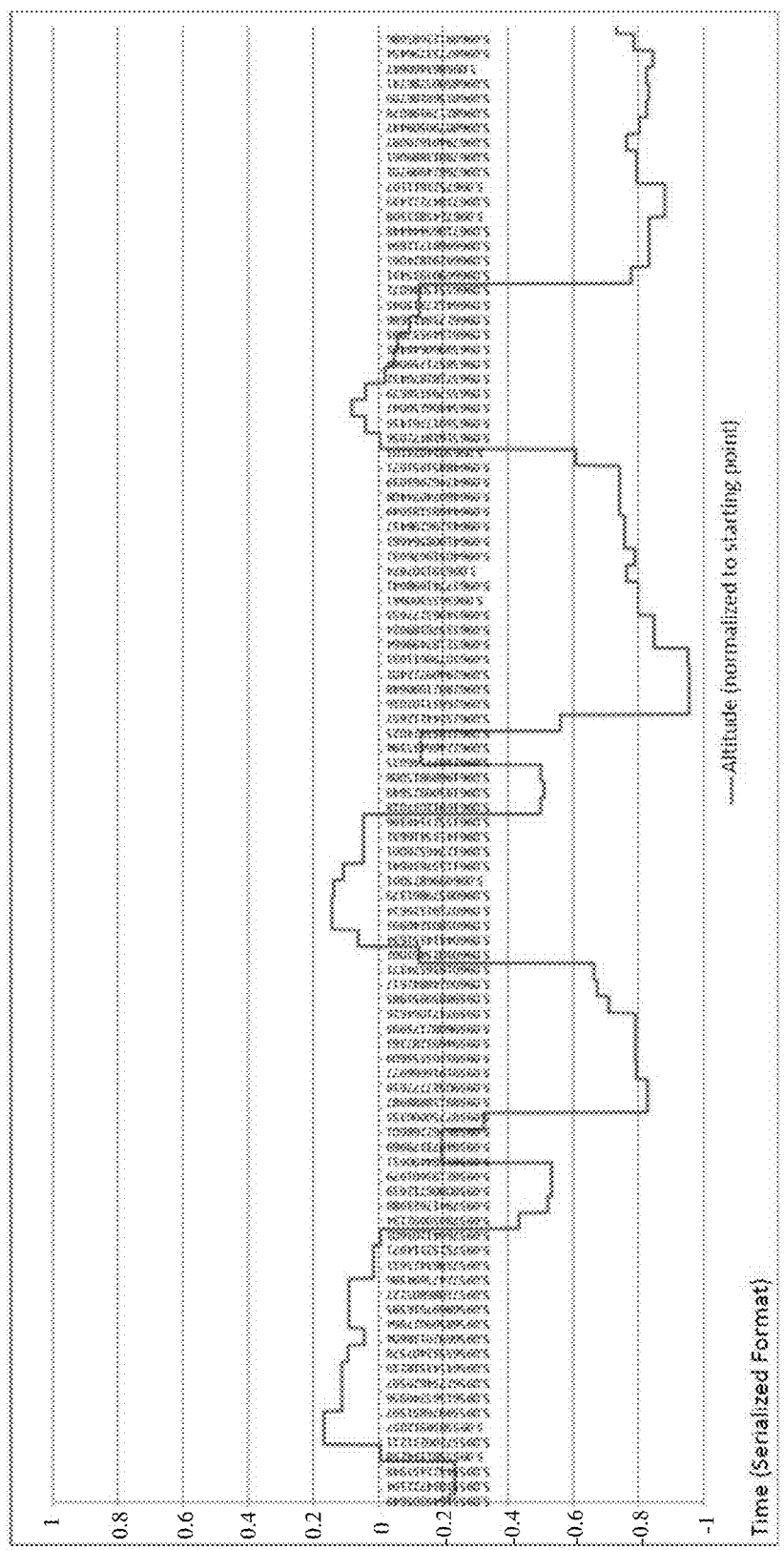
FIG. 8A is a graph which shows the collected Altitude data from a device's altimeter to show the altitude of the device during an exemplary prayer session including three prayer units.

FIG. 8A is a graph which shows the collected Altitude data from a device's altimeter to show the altitude of the device during an exemplary prayer session including three prayer units.

Figure 8B:
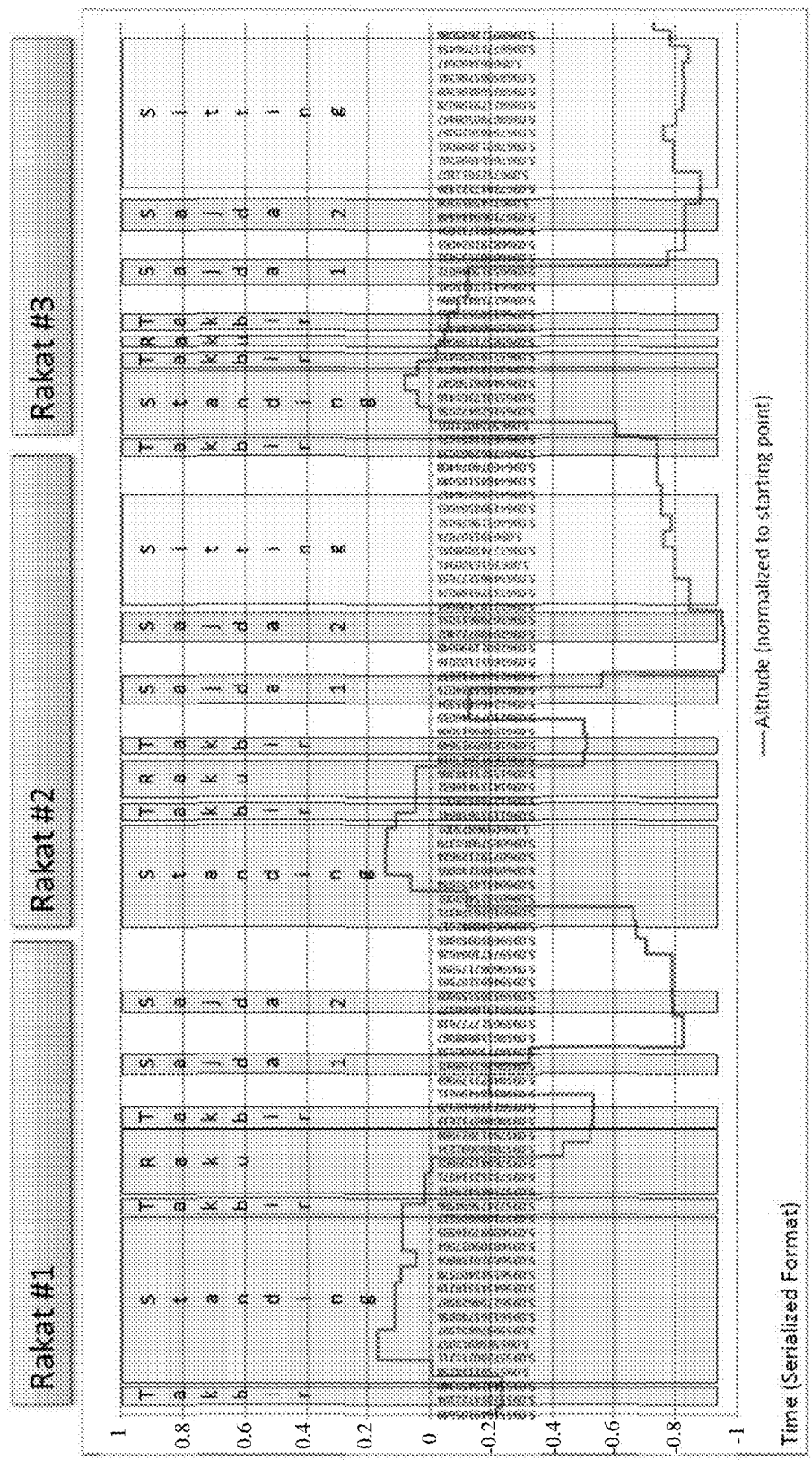
FIG. 8B is a graph which shows a coded overlay on top of the data from FIG. 8A to show the breakdown of the altitude of the device corresponding to the specific posture of the user within each prayer unit of the three prayer units in the exemplary prayer session.

FIG. 8B is a graph which shows a coded overlay on top of the data from FIG. 8A to show the breakdown of the altitude of the device corresponding to the specific posture of the user within each prayer unit of the three prayer units in the exemplary prayer session.

Figure 9A:
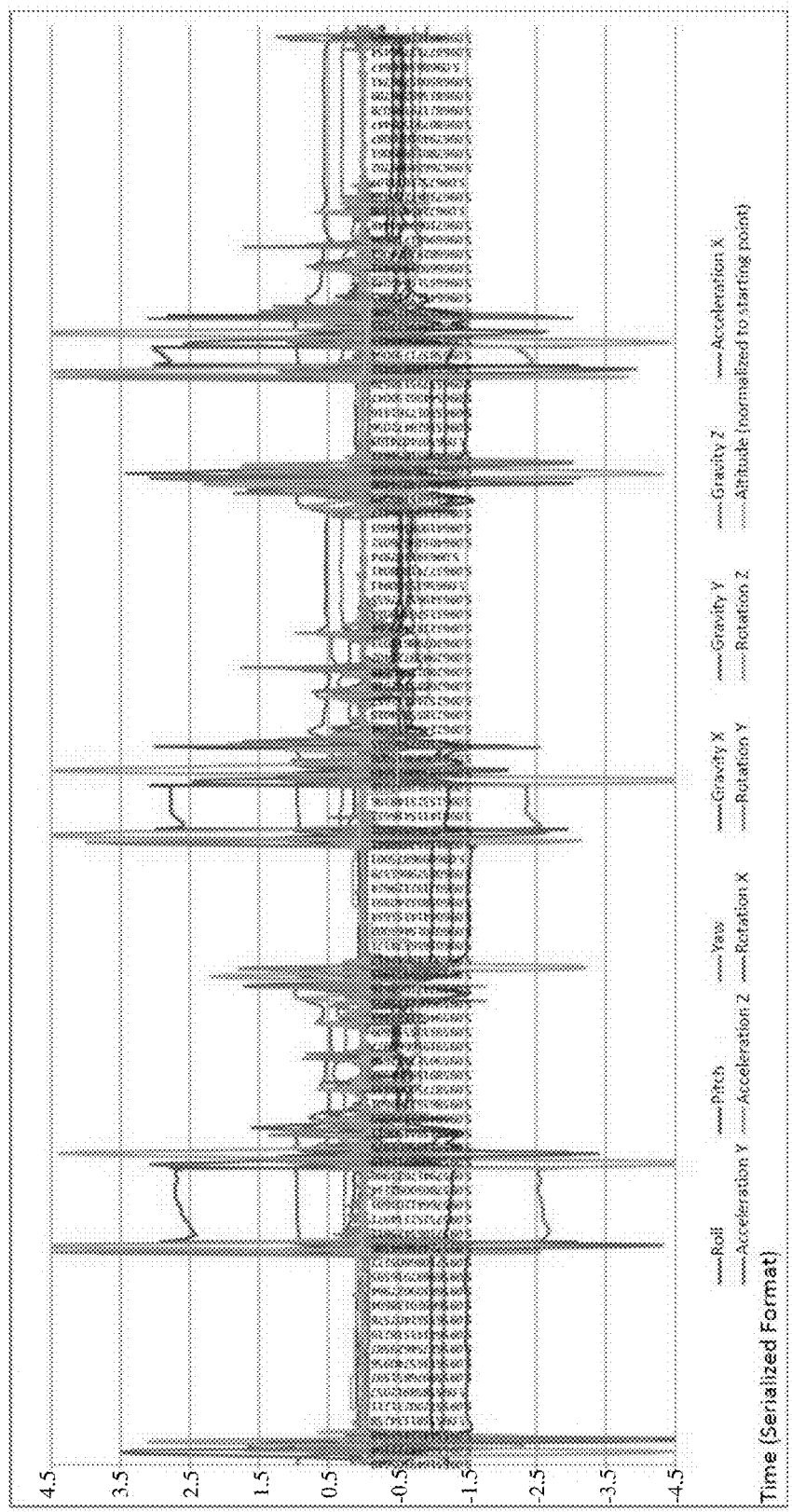
FIG. 9A is a graph which shows the combined collected data ('roll, pitch, yaw', XYZ gravity, XYZ acceleration, XYZ rotation and altitude) from a device's gyroscope, accelerometer and altimeter during an exemplary prayer session including three prayer units.

FIG. 9A is a graph which shows the combined collected data ('roll, pitch, yaw', XYZ gravity, XYZ acceleration, XYZ rotation and altitude) from a device's gyroscope, accelerometer and altimeter during an exemplary prayer session including three prayer units.

Figure 9B:
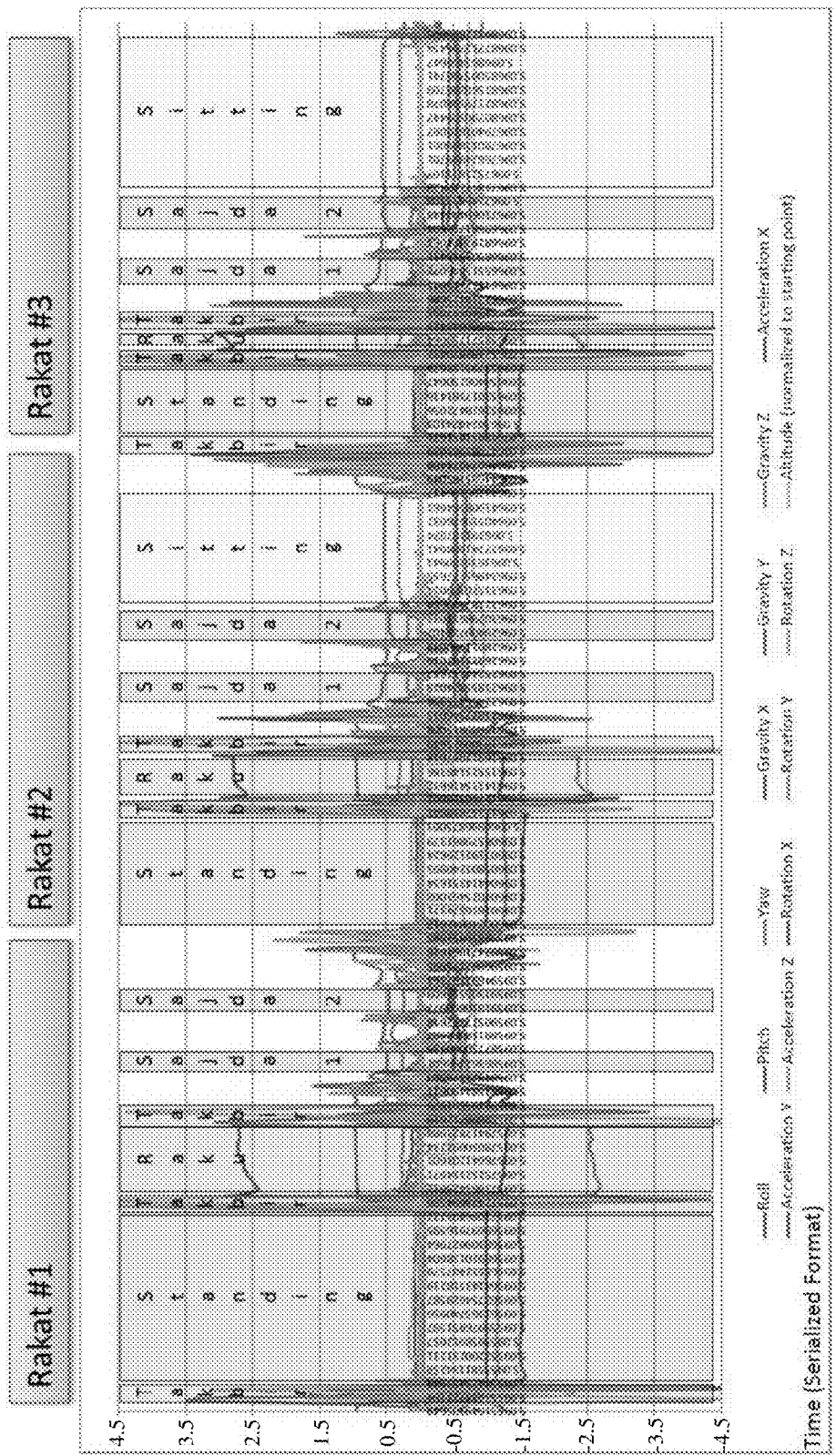
FIG. 9B is a graph which shows a coded overlay on top of the data from FIG. 8A to show the breakdown of the combined data of the device corresponding to the specific posture of the user within each prayer unit of the three prayer units in the exemplary prayer session.

FIG. 9B is a graph which shows a coded overlay on top of the data from FIG. 8A to show the breakdown of the combined data of the device corresponding to the specific posture of the user within each prayer unit of the three prayer units in the exemplary prayer session.

As can be seen from FIGS. 4A-9B, the collected data in each graph can be used to identify certain transition points when the user's prayer position changes and based on the values of the data points and the identified transition points, it can be determined which position the user is in (e.g., raising their hands at the outset of prayer (takbir), standing, bowing down (raku), prostrating (sajda), sitting, etc.).

Of note, smartphone and wearable device algorithms based on pocket versus wrist implementations are largely the same. The difference is that wearable wrist device will detect Takbir and also Raku, where the smartphone will not. The algorithm does not need to change.

The difference between the two is that the wearable wrist device and smartphone will trigger different Gyroscope data values for the various positions which will be distinctly different combination of Roll, Pitch, Yaw, and X, Y, Z gravity orientation. The accelerations values are not used to calculate the position, rather they are used to indicate the person is transitioning between various positions.

Furthermore, as data sets of user sessions are gathered, it is possible to use machine learning algorithms to decipher patterns in an individual user's motions to specifically tune the position algorithms to precisely calculate the number of Rakats (prayer units) that the user has completed and more accurately alert the user of their progress. As can be seen in FIGS. 4-9, where each graph is overlaid with specific prayer positions, the variance within the pattern of an individual person can be tuned. Calculating and understanding variances both between individuals as well as within different sessions of a specific person can make the algorithm dynamic and very accurate at an individual person level.

One or more exemplary embodiments may also be embodied as programmed commands to be executed in various computer means, and then may be recorded to a computer-readable storage medium. The computer-readable storage medium may include one or more of the programmed commands, data files, data structures, or the like. The programmed commands recorded to the computer-readable storage medium may be particularly designed or configured for one or more exemplary embodiments. Examples of the computer-readable storage medium include magnetic media including hard disks, magnetic tapes, and floppy disks, optical media including CD-ROMs and DVDs, magneto-optical media including optical disks, and a hardware apparatus designed to store and execute the programmed commands in ROM, RAM, a flash memory, and the like. The hardware apparatus may be configured to function as one or more software modules so as to perform operations of one or more exemplary embodiments.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope of the inventive concept as defined by the following claims.

The invention claimed is:

1. A method of tracking a prayer session of a device user and notifying the device user regarding prayer session activity, the method comprising:
   receiving, by at least one processor, altitude information from an altimeter of the device while the device user is engaged in the prayer session;
   determining, by the at least one processor, at least one of a prayer unit number and prayer position based on the received altitude information; and
   outputting, by the at least one processor, to a notification device to notify the device user of at least one of the determined prayer unit number and prayer position,
   wherein the determining the at least one of the prayer unit number and the prayer position comprises:
      determining a standing altitude of the user in a standing position based on the received altitude information from the altimeter;
      determining a prostration altitude by subtracting a relative difference value from the standing altitude;
      determining a current altitude from the altimeter;
      determining whether a difference between the current altitude and a previous altitude is greater than a predetermined amount; and
      based on a determination that the difference between the current altitude and the previous altitude is greater than the predetermined amount, determining whether the current altitude is within a range of the standing altitude or within a range of the prostration altitude so as to determine the at least one of the prayer unit number and the prayer position.

2. The method of claim 1, wherein the method further comprises:
reading time information from a clock of the device;
determining location information using GPS or cell towers;
determining, based on at least one of the read time information and the determined location information, at least one of a type of prayer the device user is performing, corresponding time of day, and corresponding number of prayer units for the type of prayer; and
notifying the user of at least one of the determined prayer unit number and prayer unit position based on at least one of the determined type of prayer, corresponding time of day, and corresponding number of prayer units for the type of prayer.

3. The method of claim 1, wherein the notifying comprises notifying the device user of the determined prayer unit number or prayer position using one of a visual notification, audio notification, and haptic notification.

4. The method of claim 1, further comprising:
storing user prayer activity information for each prayer session of the user; and
displaying the user prayer activity information of the prayer sessions based on a comparison between the user's current collected data and the user's historical data as well as other users' prayer activity information.

5. A non-transitory computer readable medium comprising an application for tracking a prayer session of a device user and notifying the device user regarding prayer session activity, the application comprising function of:
receiving, by at least one processor, altitude information from an altimeter of the device while the device user is engaged in the prayer session;
determining, by the at least one processor, at least one of a prayer unit number and prayer position based on the received altitude information; and
outputting, by the at least one processor, to a notification device to notify the device user of at least one of the determined prayer unit number and prayer position,
wherein the determining the at least one of the prayer unit number and the prayer position comprises:
determining a standing altitude of the user in a standing position based on the received altitude information from the altimeter;
determining a prostration altitude by subtracting a relative difference value from the standing altitude;
determining a current altitude from the altimeter;
determining whether a difference between the current altitude and a previous altitude is greater than a predetermined amount; and
based on a determination that the difference between the current altitude and the previous altitude is greater than the predetermined amount, determining whether the current altitude is within a range of the standing altitude or within a range of the prostration altitude so as to determine the at least one of the prayer unit number and the prayer position.

6. The non-transitory computer readable medium of claim 5, wherein the application further comprises functions of
reading time information from a clock of the device;
determining location information using GPS or cell towers;
determining, based on at least one of the read time information and the determined location information, at least one of a type of prayer the device user is performing, corresponding time of day, and corresponding number of prayer units for the type of prayer; and
notifying the user of at least one of the determined prayer unit number and prayer unit position based on at least one of the determined type of prayer, corresponding time of day, and corresponding number of prayer units for the type of prayer.

7. The non-transitory computer readable medium of claim 5, wherein the notifying comprises notifying the device user of the determined prayer unit number or prayer position using one of a visual notification, audio notification, and haptic notification.

8. The non-transitory computer readable medium of claim 5, wherein the application further comprises functions of
storing user prayer activity information for each prayer session of the user; and
displaying the user prayer activity information of the prayer sessions based on a comparison between the user's current collected data and the user's historical data as well as other users' prayer activity information.

9. A method of tracking a prayer session of a device user and notifying the device user regarding prayer session activity, the method comprising:
receiving, by at least one processor, motion information from an accelerometer of the device while the device user is engaged in the prayer session;
receiving, by the at least one processor, altitude information from an altimeter of the device while the device user is engaged in the prayer session;
receiving, by the at least one processor, position information from a gyroscope of the device while the device user is engaged in the prayer session;
reading, by the at least one processor, time information from a clock of the device;
determining, by the at least one processor, location information using GPS or cell towers;
determining, by the at least one processor, based on at least one of the read time information and the determined location information, at least one of a type of prayer the device user is performing and corresponding number of prayer units for the type of prayer;
determining, by the at least one processor, at least one of a prayer unit number and prayer position based on one or more of the received motion information, altitude information, and position information; and
outputting, by the at least one processor, to a notification device to notify the device user of at least one of the determined prayer unit number and prayer position based on at least one of the determined type of prayer and corresponding number of prayer units for the type of prayer,
wherein the determining the at least one of the prayer unit number and the prayer position comprises:
determining whether an acceleration value from the motion information is less than or equal to a threshold value;
based on a determination that the acceleration value from the motion information is less than or equal to the threshold value, determine whether a position value from the position information matches one of a plurality of prayer positions so as to determine the at least one of the prayer unit number and the prayer position, and
wherein the determining the at least one of the prayer unit number and the prayer position based on the altitude information comprises:

determining a standing altitude of the user in a standing position based on the received altitude information from the altimeter;

determining a prostration altitude by subtracting a relative difference value from the standing altitude;

determining a current altitude from the altimeter;

determining whether a difference between the current altitude and a previous altitude is greater than a predetermined amount; and based on a determination that the difference between the current altitude and the previous altitude is greater than the predetermined amount, determining whether the current altitude is within a range of the standing altitude or within a range of the prostration altitude so as to determine the at least one of the prayer unit number and the prayer position.

10. A non-transitory computer readable medium comprising an application for tracking a prayer session of a device user and notifying the device user regarding prayer session activity, the application comprising function of:

receiving, by at least one processor, motion information from an accelerometer of the device while the device user is engaged in the prayer session;

receiving, by the at least one processor, altitude information from an altimeter of the device while the device user is engaged in the prayer session;

receiving, by the at least one processor, position information from a gyroscope of the device while the device user is engaged in the prayer session;

reading, by the at least one processor, time information from a clock of the device;

determining, by the at least one processor, location information using GPS or cell towers;

determining, by the at least one processor, based on at least one of the read time information and the determined location information, at least one of a type of prayer the device user is performing and corresponding number of prayer units for the type of prayer;

determining, by the at least one processor, at least one of a prayer unit number and prayer position based on one or more of the received motion information, altitude information, and position information; and outputting, by the at least one processor, to a notification device to notify the device user of at least one of the determined prayer unit number and prayer position based on at least one of the determined type of prayer and corresponding number of prayer units for the type of prayer, wherein the determining the at least one of the prayer unit number and the prayer position based on the received motion information and the position information comprises:

determining whether an acceleration value from the motion information is less than or equal to a threshold value;

based on a determination that the acceleration value from the motion information is less than or equal to the threshold value, determine whether a position value from the position information matches one of a plurality of prayer positions so as to determine the at least one of the prayer unit number and the prayer position; and wherein the determining the at least one of the prayer unit number and the prayer position based on the altitude information comprises:

determining a standing altitude of the user in a standing position based on the received altitude information from the altimeter;

determining a prostration altitude by subtracting a relative difference value from the standing altitude;

determining a current altitude from the altimeter;

determining whether a difference between the current altitude and a previous altitude is greater than a predetermined amount; and based on a determination that the difference between the current altitude and the previous altitude is greater than the predetermined amount, determining whether the current altitude is within a range of the standing altitude or within a range of the prostration altitude so as to determine the at least one of the prayer unit number and the prayer position.

* * * * *